United States Patent
Levy et al.

(10) Patent No.: US 6,540,654 B2
(45) Date of Patent: Apr. 1, 2003

(54) CAROTENOID ESTERS

(76) Inventors: Luis W. Levy, c/o Inexa, Industria Extractora C.A., P.O. Box 17-03-4581, Quito (EC); Richard H. Binnington, 17 Castle Road, Sandal Wakefield West Yorkshire, WF2 7LU (GB); Anthony S. Tabatznik, 75 Sheringham, Queensmead, St John's Wood Park, London, NW8 6RB (GB)

( * ) Notice: Subject to any disclaimer, the term of this patent is extended or adjusted under 35 U.S.C. 154(b) by 0 days.

(21) Appl. No.: 10/081,085

(22) Filed: Feb. 22, 2002

(65) Prior Publication Data

US 2002/0169334 A1 Nov. 14, 2002

Related U.S. Application Data

(60) Provisional application No. 60/270,817, filed on Feb. 23, 2001, and provisional application No. 60/347,443, filed on Jan. 11, 2002.

(51) Int. Cl.⁷ .............................................. C07C 57/00
(52) U.S. Cl. ....................... 584/224; 584/223; 584/229; 584/230
(58) Field of Search ................. 584/223, 224, 584/229, 230

(56) References Cited

U.S. PATENT DOCUMENTS

| | | |
|---|---|---|
| 2,768,198 A | 10/1956 | Marbet et al. |
| 3,206,316 A | 9/1965 | Kläui |
| 5,536,504 A | 7/1996 | Eugster et al. |
| 5,959,138 A | 9/1999 | Torres-Cardona et al. |
| 6,191,293 B1 | 2/2001 | Levy |

FOREIGN PATENT DOCUMENTS

| | | |
|---|---|---|
| DE | 199 50 327 A1 | 4/2000 |
| WO | WO 98/45241 A2 | 10/1998 |

OTHER PUBLICATIONS

Chew, et al., "Effects of Lutein from Marigold Extract on Immunity and Growth of Mammary Tumors in Mice", *Anticancer Research*, vol. 16, pp. 3689–3694, (1996).

(List continued on next page.)

*Primary Examiner*—Deborah D. Carr
(74) *Attorney, Agent, or Firm*—Akin, Gump, Strauss, Hauer & Feld, L.L.P.

(57) ABSTRACT

Monoesters, diesters and polyesters are provided wherein both the acid-derived moiety and the alcohol-derived moiety of the esters are carotenoid compounds. The synthetic ester linkage between two or more carotenoids provides new compounds in which the similar and complementary properties of the individual carotenoids are combined. The new all-carotenoid esters may be useful as antioxidants, therapeutic agents, pigmenting ingredients in poultry feed or as coloring agents for fats. The polyesters have the potential to act as molecular wires with unique electrical conductance characteristics. The all-carotenoid esters may be prepared from the esterification of at least one hydroxy carotenoid with at least one carboxylic carotenoid, or via the reaction of the acid chloride of a carboxylic carotenoid with a hydroxy carotenoid. Preferred hydroxy carotenoids include lutein, zeaxanthin, cryptoxanthin, violaxanthin, carotene diol, hydroxy carotene, hydroxylycopene, alloxanthin and dehydrocryptoxanthin. Preferred carboxylic carotenoids include bixin, norbixin, β-apo-8-carotenoic acid, crocetin, diapocarotenoic acid, carboxylcarotene and azafrin.

3 Claims, 2 Drawing Sheets

Lutein Monobixinate

OTHER PUBLICATIONS

Landrum, et al., "Lutein, Zeaxanthin, and the Macular Pigment", *Archives of Biochemistry and Biophysics*, 385:1, pp. 28–40, (Jan. 1, 2001).

Krinsky, "The Biological Properties of Carotenoids", *Pure & Appl. Chem.*, 66:5, pp. 1003–1010, (1994).

Straub, "Key to Carotenoids", *Institute of Organic Chemistry University of Berne*, $2^{nd}$ and Revised Edition, (1987).

ALAM, et al., "Fatty Acid Composition of the Xanthophyll Esters of *Tagetes ercta* Petals", *Lipids*, 3:2, pp. 183–184, (Mar. 1968).

Partali, et al., "Stable, Highly Unsaturated Glycerides—Enzymatic Synthesis with a Carotenoic Acid", *Angew. Chem. Int. Ed. Engl.*, 35:3, pp. 329–331, (1996).

Larsen, et al., "Combination of Vitamin E with a Carotenoid: α–Tocopherol and Trolox Linked to β–Apo–8'–carotenoic Acid", *Chem. Eur. J.*, 4:1, pp. 113–117, (1998).

Humeau, et al., "Enzymatic Esterification of Bixin by L–ascorbic Acid", *Biotechnol. Lett.*, 22:2, (2000) Abstract Only.

Gann, et al., "Lower Prostate Cancer Risk in Men with Elevated Plasma Lycopene Levels: Results of a Prospective Analysis", *Cancer Research*, vol. 59, pp. 1225–1230, (Mar. 15, 1999).

Ziegler, "Carotenoids, Cancer, and Clinical Trials", *Annals of the New York Academy of Sciences*, vol. 691: "Carotenoids in Human Health", pp. 111–119, (1993).

Roth, "Current Chemotherapy and Infectious Diseases", (Nelson, et al., Eds. American Society of Microbiology: Washington, D.C., pp. 1503–1505, (1980). [Out of Print and No Longer Available].

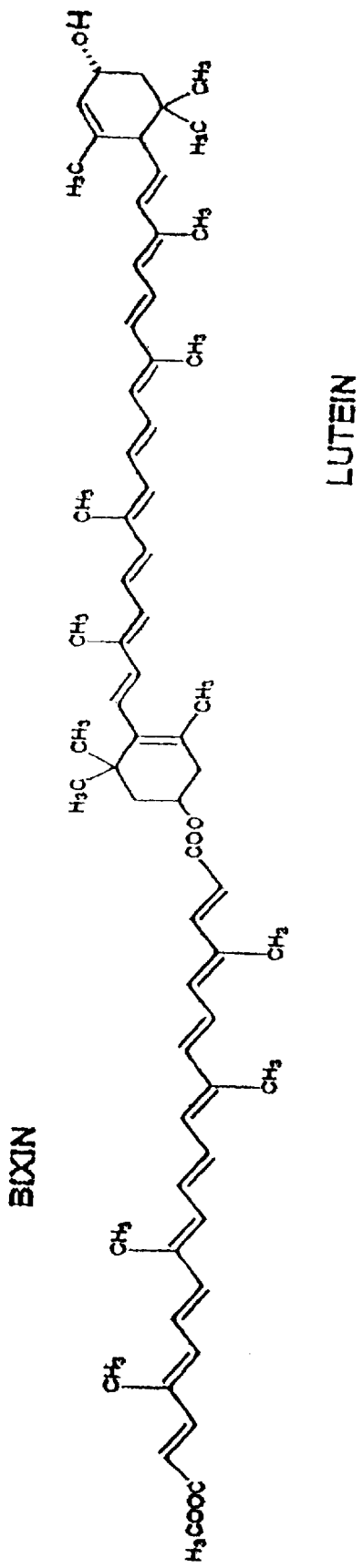
Figure 1: Lutein Monobixinate

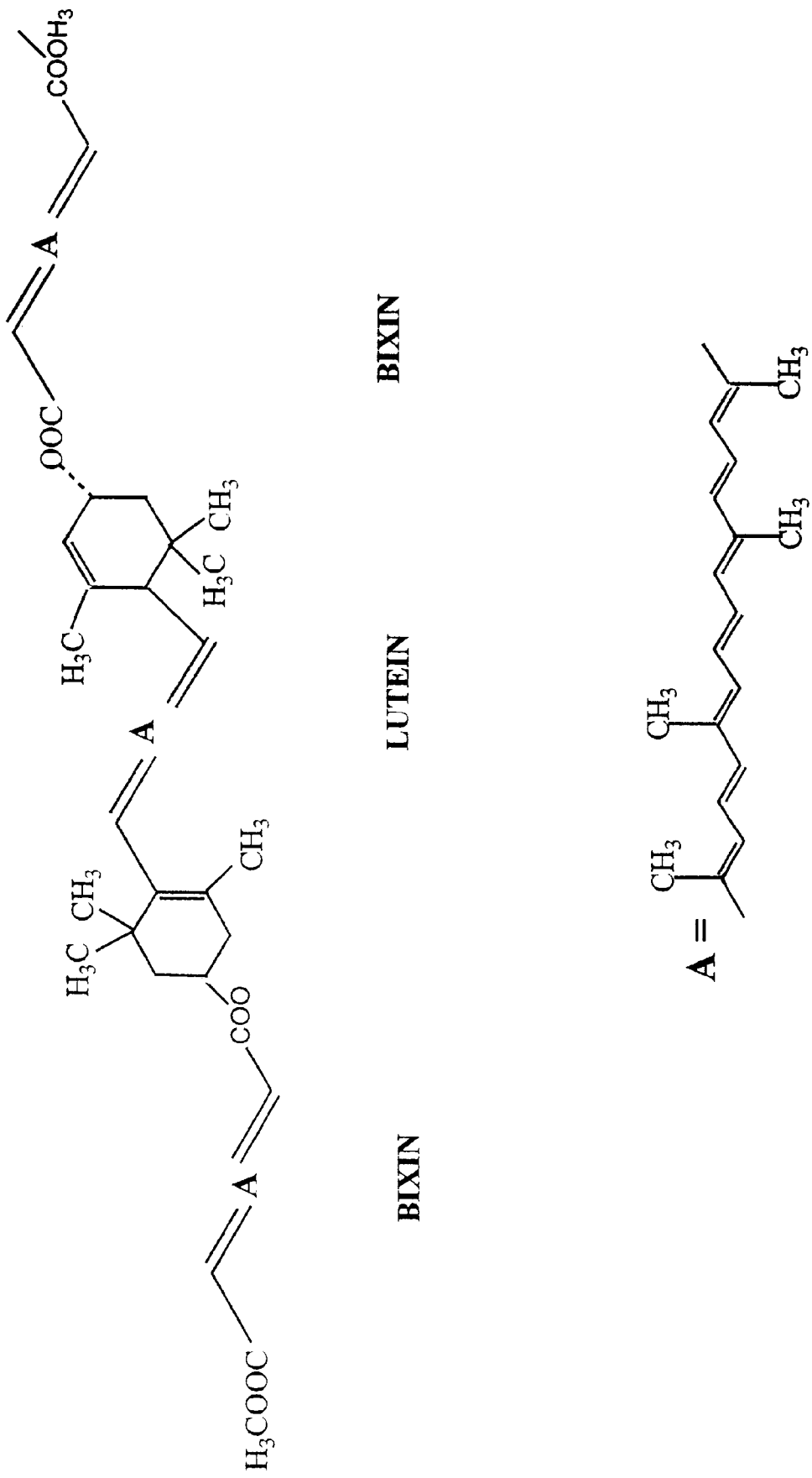
Figure 2: Lutein dibixinate

CAROTENOID ESTERS

CROSS-REFERENCE TO RELATED APPLICATIONS

This application claims the benefit of U.S. Provisional Patent Applications Nos. 60/270,817, filed Feb. 23, 2001 and No. 60/347,443 filed Jan. 11, 2002.

BACKGROUND OF THE INVENTION

The carotenoids are important natural products which are involved in the photosynthetic process of plants. Carotenoids are used as nutritional supplements for animals and humans, as well as in food colorants and cosmetics. Although carotenoids are important for health, animals and humans cannot produce them, and these compounds must thus be obtained through diet from fruits and vegetables.

Several properties of the carotenoids make them important for the health of both animals and humans. For example, these compounds are antioxidants with important quenching effects on free radicals. They protect living tissues against a variety of diseases, either directly or as immunopotentiators. Additionally, carotenoids are involved in gap-junction communication among living cells. Recent epidemiological evidence has suggested an inverse relationship between the consumption of fruits and vegetables with high carotenoid content and the incidence of several types of cancers. Specifically, β-carotene, lutein and lycopene have been shown to exhibit a cancer-prevention effect (M. M. Mathews-Roth, *Current Chemotherapy and Infectious Diseases* (J. D. Nelson and C. Grassi, Eds, Am. Soc. Microbiol., Washington D.C.:1503–1505(1980)); B. P. Chew et al, *Anticancer Research* 16:3689–3694 (1996); P. H. Gann et al, *Cancer Res.* 59:1225–1230 (1999)).

Additionally, several carotenoids, such as lutein and zeaxanthin, have specific functions in the retina of the eye to assure healthy vision in several animal species, including humans (J. D. Landrum et al., *Archives Biochem. Biophys.* 385(1):28–40(2001)). Finally, some carotenoids have provitamin A activity, whereas others control reproduction and fertility, upregulate the Connexin43 gene, decrease the risk of degenerative disease and prevent coronary heart disease (N. Krinsky, *Pure and Appl. Chem.* 66(5):1003-1010 (1994)).

From a chemical standpoint, carotenoids may be classified by their functional groups into several categories (see *Key to Carotenoids,* 2nd enlarged and revised edition, H. Pfander et al, Birkhäuser Verlag, Basel, 1987). These include hydrocarbon carotenoids such as β-carotene and lycopene, monohydroxy carotenoids such as β-cryptoxanthin, dihydroxy carotenoids such as lutein and zeaxanthin, polyhydroxy carotenoids such as β,β-carotene triol, epoxycarotenoids such as violaxanthin and antheraxanthin, carbonyl carotenoids such as echinenone, capsanthin, canthaxanthin and astaxanthin, and carotenoid acids such as bixin and crocetin.

Esters with a carotenoid as the alcohol-derived moiety are well known. For example, the monoesters and diesters of lutein and zeaxanthin with palmitic acid, myristic acid and stearic acid occur in nature. They are also known as the "xanthophylls" of the flowers and leaves of most plants (Alam, *Lipids,* 3:183 (1968)). These esters are also prepared commercially, as described, for example, in U.S. Pat. No. 6,191,293 of Levy via the extraction of the flowers of the marigold plant (*Tagetes erecta*) with subsequent purification.

Additionally, some esters containing a carotenoid as the alcohol-derived moiety have been prepared synthetically. For example, the valerate, laurate, oleate, linoleate and caproate esters of the carotenoids zeaxanthin and isozeaxanthin have been described in U.S. Pat. No. 5,536,504 of Eugster, et al. Short chain organic acid diesters of lutein and zeaxanthin have also been described in U.S. Pat. No. 5,959,138 of Torres-Cardona, et al.

Esters containing a carotenoid as the acid-derived moiety are also well known. Whereas many occur in nature ("*Key to Carotenoids*"), other esters of this type have been prepared by synthesis. For example, U.S. Pat. No. 2,768,198 of Marbet, et al. describes the preparation of esters of bixin and norbixin with amyl alcohol, octyl alcohol and Vitamin A.

Finally, glycerides with a carotenoid acid have been prepared by enzymatic catalysis (Partali et al, *Angew. Chem Int. Ed. Engl.* 35:329–330 (1996)). The reaction of β-apo-8'-carotenoic acid with Vitamin E yields α-tocopheryl-β-8'-carotenoate as described by Larsen et al (*Chem. Eur. J.* 4:113–117 (1998)). Additionally, the enzymatic esterification of bixin using L-ascorbic acid, which contains two alcoholic OH groups, as the alcohol moiety has been reported by Humeau et al (*Biotechnol. Lett.* 22:155–168 (2000)).

In summary, although many esters containing carotenoid components are known, all of the known carotenoid esters contain a non-carotenoid component as the alcohol-derived moiety or the acid-derived moiety.

BRIEF SUMMARY OF THE INVENTION

This invention is directed to esters comprising at least one alcohol-derived moiety and at least one acid-derived moiety, wherein the at least one alcohol-derived moiety comprises a hydroxy carotenoid selected from the group consisting of monohydroxy carotenoids, dihydroxy carotenoids, and polyhydroxy carotenoids, and wherein the acid-derived moiety comprises a carboxylic carotenoid selected from the group consisting of monocarboxylic carotenoids, dicarboxylic carotenoids, and polycarboxylic carotenoids. Preferred hydroxy carotenoids include lutein, zeaxanthin, cryptoxanthin, violaxanthin, carotene diol, hydroxy carotene, hydroxylycopene, alloxanthin and dehydrocryptoxanthin. Preferred carboxylic carotenoids include bixin, norbixin, β-apo-8-carotenoic acid, crocetin, diapocarotenoic acid, carboxylcarotene and azafrin.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a structural formula of lutein monobixinate; and

FIG. 2 is a structural formula of lutein dibixinate.

DETAILED DESCRIPTION OF THE INVENTION

This invention is directed to a new class of esters in which both the acid-derived moiety and the alcohol-derived moiety are carotenoids. For the purposes of this disclosure, the terms "alcohol-derived moiety" and "alcohol moiety" may both be understood to refer to the fragment of the ester molecule which is derived from an alcohol. Similarly, the terms "acid-derived moiety" and "acid moiety" both refer to the fragment of the ester molecule which is derived from a carboxylic acid.

The new class of esters, which includes monoesters, diesters and polyesters, is substantially different from known esters because both the alcohol and the acid moieties are carotenoid compounds. The esters according to the present invention may thus be called "hybrid carotenoid esters" or "all-carotenoid esters." These all-carotenoid esters show the combined color characteristics and the combined antioxidant potential of both moieties which makes them superior to the individual carotenoid components. Their exceptionally high antioxidant potential and outstanding fat solubility make the all-carotenoid esters promising coloring agents, efficient antioxidants, pharmaceutical agents with high biological activity, and even polymeric products exhibiting unique characteristics of electrical conduction.

The all-carotenoid esters according to the present invention are prepared from the combination of at least one hydroxy carotenoid and at least one carboxylic carotenoid. Hydroxy carotenoids which may be used to form these esters may be monohydroxy carotenoids, dihydroxy carotenoids, or polyhydroxy carotenoids. While not meant to be limiting, exemplary hydroxy carotenoids are shown in Table 1. Preferred hydroxy carotenoids according to the present invention include lutein, zeaxanthin, cryptoxanthin, violaxanthin, carotene diol, hydroxycarotene, hydroxylycopene, alloxanthin and dehydrocryptoxanthin. Hydroxy carotenoids which are more preferred include lutein, zeaxanthin, cryptoxanthin and violaxanthin, and the most preferred carotenoids are lutein, zeaxanthin, and dehydrocryptoxanthin.

TABLE 1

Examples of hydroxy carotenoids

| | |
|---|---|
| Alloxanthin | Hydroxycarotenones |
| Apocarotenol | Hydroxyechinenones |
| Astacene | Hydroxylycopene |
| Astaxanthin | Lutein |
| Capsanthin | Lycoxanthin |
| Capsorubin | Neurosporine |
| Carotenediols | Phytoene |
| Carotenetriols | Phytofluoene |
| Carotenols | Rodopin |
| Citranaxanthin | Spheroidine |
| Cryptoxanthin | Torulene |
| Decaprenoxanthin | Violaxanthin |
| Denethylated-spheroidine | Zeaxanthin |
| Epilutein | |
| Fucoxanthin | |

The carboxylic carotenoid according to the present invention may be a monocarboxylic carotenoid, dicarboxylic carotenoid or polycarboxylic carotenoid. While not meant to be limiting, exemplary carboxylic carotenoids are shown in Table 2. Preferred carboxylic carotenoids include bixin, norbixin, β-apo-8'-carotenoic acid, crocetin, diapocarotenoic acid, carboxylcarotene, and azafrin. More preferred carboxylic carotenoids include bixin, norbixin, crocetin and β-apo-8'-carotenoic acid, whereas bixin, norbixin, and β-apo-8'-carotenoic acid are the most preferred carboxylic carotenoids.

TABLE 2

Examples of carboxylic carotenoids

| | |
|---|---|
| Apocarotenoic acid | Crocetin |
| β-apo-8'-carotenoic acid | Diapocarotenoic acid |
| Azafrin | Neurosporaxanthin |
| Bixin | Norbixin |
| Carboxylcarotenes | Lycopenoic acid |

Depending on the particular carotenoid components and the stoichiometric proportion of the reactant carotenoids used for the esterification reaction, the resulting carotenoid ester may be a dicarotenoid monoester, a tricarotenoid diester or a polycarotenoid polyester. For example, dicarotenoid monoesters originate from the reaction of one molecule of a dihydroxy carotenoid, such as lutein or zeaxanthin, with one molecule of a monocarboxylic carotenoid, such as bixin. Tricarotenoid diesters are the result of the reaction of one molecule of a dihydroxy carotenoid with two molecules of a monocarboxylic carotenoid. Finally, polycarotenoid polyesters result from the reaction of several molecules of a dihydroxy carotenoid with several molecules of a dicarboxylic carotenoid, such as norbixin. Examplary possible combinations of carotenoid esters of lutein with bixin, norbixin and apocarotenoic acid are shown in Table 3.

TABLE 3

Types of all-carotenoid esters

| Alcohol Moiety | Acid Moiety | Ester |
|---|---|---|
| Lutein (one mol) | Bixin (one mol) | Lutein monobixinate |
| Lutein (one mol) | Bixin (one mol) | Dehydrocryptoxanthin Monobixinate |
| Lutein (one mol) | Bixin (two mol) | Lutein dibixinate |
| Lutein (one mol) | Norbixin (one mol) | Lutein norbixinate |
| Lutein (one mol) | Norbixin (two mols) | Lutein dinorbixinate |
| Lutein (two mols) | Norbixin (one mol) | Dilutein norbixinate |
| Lutein (molar excess) | Norbixin (excess) | Polylutein polynorbixinate |
| Lutein (one mol) | Apocarotenoic Acid (one mol) | Lutein monoapocarotenoate |
| Lutein (one mol) | Apocarotenoid Acid (two mols) | Lutein di-apocarotenoate |

The structural formulas of two esters formed from the reaction of lutein and bixin, lutein monobixinate and lutein dibixinate, are shown in FIGS. 1 and 2, respectively. Interestingly, the second ester product shown in Table 3 is the bixinate of anhydrolutein or 3',4'-dehydrocryptoxanthin, which was obtained as an unexpected byproduct of the reaction between lutein and bixin. This compound was formed by a dehydration reaction of the unreacted hydroxyl group of lutein.

The esterification of the dicarboxylic carotenoid norbixin with the dihydroxy carotenoid lutein proceeds on both sides of both reactant molecules to form a polymeric ester, comparable to the well-known polyester material obtained by esterification of ethylene glycol with terephthalic acid, which is spun into a fiber called Dacron™. The polycarotenoid polyesters of the present invention not only have unique antioxidant and light absorbing properties, but because of their highly unsaturated polymeric nature, they are plastics with unique characteristics of electrical conduction. They may be used as "molecular wires" for electrical transmission and as semiconducting polymers in novel applications for fuel cells, plastic circuitry, light-emitting devices and transistors, for example.

The esters in which both the acid moiety and the alcohol moiety are carotenoids may be prepared by any method known in the art for esterification, including those known in the general chemistry laboratory and in the industrial setting for esterifying alcohols with acids. The first method comprises reacting at least one hydroxy carotenoid directly with at least one carboxylic carotenoid. For example, the esterification of a hydroxy carotenoid with a carboxylic carotenoid is possible by known catalytic techniques, as for example through carbodiimide coupling in the presence of dimethylaminopyridine. Enzymatic esterification with a lipase is yet another way of preparing these carotenoid esters.

In a preferred embodiment, an acid chloride of at least one carboxylic carotenoid is used as the intermediate for the esterification. The acid chloride may be prepared by any method known in the art such as via the known reactions with phosphorus tri- or pentachloride, with thionyl chloride, or with the highly-reacting formyl chloride (McGill U., *Tetrahedron Letters* (1997) 38(37):6489). In a more preferred embodiment, the acid chloride is prepared from the reaction of the carboxylic carotenoid with oxalyl chloride. This acid chloride is then reacted with at least one hydroxy carotenoid to form the desired carotenoid ester.

The invention will best be described in more detail with respect to the following non-limiting examples.

EXAMPLE 1

Lutein monobixinate, as shown in FIG. 1, was synthesized according to the following procedure. Bixin (500 mg, 1.27 mmol) was converted to bixinoyl chloride in dry dichloromethane (50 mL) by the addition of oxalyl chloride (500 μL, 5.25 mmol) and N,N-dimethylformamide (1 drop). The mixture was stirred at room temperature for 1 hour and then was evaporated to dryness under reduced pressure to yield bixinoyl chloride.

Bixinoyl chloride (4 mg, 25 μmol) was mixed with lutein (1 mg, 1.76 μmol) in 1 mL of dry toluene. Pyridine (1 drop) was added and the mixture was stirred at room temperature for 6 days. The esterification reaction was monitored by thin-layer chromatography (TLC) on a silica plate with 20% ethyl acetate in dichloromethane as the developing phase. The reaction was considered complete when the spot of the reactant lutein (Rf=0.2) had largely disappeared and a new, less polar, red spot had appeared which ran almost at the solvent front (Rf=0.95).

At this stage, the mixing was stopped and the reaction mixture was evaporated under reduced pressure. The dry residue was dissolved in diethyl ether (2 mL) and chromatographed on a silica column with diethyl ether as the eluent. The front running material was collected and evaporated under reduced pressure to give lutein monobixinate, which was purified by column chromatography on silica.

Analysis of the product by TLC on silica with 20% ethyl acetate in dichloromethane gave a single spot of Rf=0.95. $^1$H Nuclear Magnetic Resonance (NMR) analysis on a Brucker AC2SO at 250 MHz in $CDCl_3$ showed the methyl ester resonance of bixin at 3.75 ppm and the double bond doublets of bixin at 7.4 ppm and 7.95 ppm. The lutein signals were observed at 3.9 ppm and 4.19 ppm, as well as the aliphatic proton resonances at 0.7–1.9 ppm. The upfield movement of the lutein signal from 3.9 ppm to 3.15 ppm is indicative of the change from the free hydroxyl to the coupled ester. The purified product thus contained the ester formed from the combination of bixin and lutein. The mass spectrum obtained using the APCI technique (Atmospheric Pressure Chemical Ionization) showed a peak at 944 consistent with lutein monobixinate ($C_{65}H_{84}O_5$).

EXAMPLE 2

Lutein dibixinate, as shown in FIG. 2, was prepared according to the following process. Bixin (550 mg, 1.39 mmol) was converted to bixinoyl chloride in dry toluene (10 mL) by the addition of oxalyl chloride (1 mL, 10.5 mmol) and refluxed under nitrogen for 1 hour to give a blood-red solution. The mixture was allowed to cool slightly and then evaporated to dryness under reduced pressure to yield bixinoyl chloride.

Bixinoyl chloride (8 mg, 19.4 μmol) was mixed with lutein (1 mg, 1.76 μmol) in 1 mL of dry toluene. A mixture of pyridine and 4-N,N-dimethylamino pyridine (2 drops) was added and the mixture refluxed for 8 hours. The esterification reaction was monitored using TLC on a silica plate with 20% ethyl acetate in dichloromethane as the developing phase. During the reaction, the spot of the reactant lutein (Rf=0.2) had largely disappeared and two new, less polar, red spots had appeared which ran almost at the solvent front (lutein monobixinate Rf=0.95 and lutein dibixinate Rf=0.98). As the reaction went to completion, only the spot with Rf=0.98 remained. At this stage the mixture was evaporated under reduced pressure. The dry residue was dissolved in diethyl ether (2 mL) and chromatographed on a silica column with elution by diethyl ether. The front running material was collected and evaporated under reduced pressure to give lutein monobixinate.

Analysis of the ester by TLC on silica developed with 20% ethyl acetate in dichloromethane gave a single spot of Rf=0.99; $^1$H NMR analysis (Brucker 250 MHz, $CDCl_3$) showed resonances at 3.7 ppm (double intensity bixin methyl ester resonance) and 0.6–1.6 ppm (lutein resonances). The mass spectrum determined by APCI showed a peak with mass 1323 consistent with lutein dibixinate ($C_{90}H_{112}O_8$).

EXAMPLE 3

Lutein mono-β-apo-8'-carotenoate was prepared as follows. The acid chloride of β-apo-8'-carotenoic acid was prepared in the same way as was the bixinoyl chloride of Example 2. The acid chloride (1.03 g, 2.5 mmol) was dissolved in benzene (10 mL). To this was added a solution of lutein (3.7 g, 6.55 mmol) and pyridine (1.2 mL, 12.8 mmol) in benzene (10 mL) under argon. The reaction was stirred at room temperature for 3 days.

The reaction mixture was diluted with ether (80 mL), washed with dilute hydro-chloric acid (0.5M, 2×50 mL), dried ($Na_2SO_4$) and evaporated. Dry flash chromatography (loading with dichloromethane and eluting with 20%, 40% and 60% ethyl acetate in light petroleum) yielded a product which, by mass spectrometry, showed a peak at mass 808 consistent with the ester lutein mono-β-apo-8'-carotenoate ($C_{55}H_{68}O_5$).

All of the new all-carotenoid esters may be useful coloring agents for fats due to their high oil solubility. Additionally, the molecular combination of these carotenoids may also increase the chemopreventive anti-cancer activity of the individual carotenoid components and protect against a variety of pathological conditions. Finally, they may be useful antioxidants due to the combination and synergistic potentiation of the antioxidant action of their carotenoid components. For example, lutein dibixinate contains 29 carbon-carbon double bonds and 4 carbon-oxygen double bonds, 31 of which are of the conjugated type. This all-carotenoid diester is one of the most highly unsaturated compounds known, exhibiting unprecedented light absorbing and antioxidant properties.

The mono-, di- and poly-all carotenoid esters according to the present invention are thus novel compounds because they contain at least two carotenoid moieties. By combining at least two carotenoids into a single compound via a synthetic ester linkage, the similar and complementary properties of the individual carotenoids are maximized. These all-carotenoid esters exhibit significantly greater antioxidant and physiological effects than the sum of the individual activities of the component carotenoids. As a result, the new all-carotenoid esters may be useful as therapeutic agents, pigmenting ingredients in poultry feed and as coloring agents for fats. Additionally, all-carotenoid polyesters may act as molecular wires exhibiting unique electrical conductance characteristics.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An ester comprising at least one alcohol-derived moiety and at least one acid-derived moiety, wherein the at least one alcohol-derived moiety comprises a hydroxy carotenoid selected from the group consisting of monohydroxy carotenoids, dihydroxy carotenoids, and polyhydroxy carotenoids, and wherein the at least one acid-derived moiety comprises a carboxylic carotenoid selected from the group consisting of monocarboxylic carotenoids, dicarboxylic carotenoids, and polycarboxylic carotenoids.

2. The ester according to claim 1, wherein the hydroxy carotenoid is selected from the group consisting of lutein, zeaxanthin, cryptoxanthin, violaxanthin, carotene diol, hydroxycarotene, hydroxylycopene, alloxanthin and dehydrocryptoxanthin.

3. The ester according to claim 1, wherein the carboxylic carotenoid is selected from the group consisting of bixin, norbixin, β-apo-8'-carotenoid acid, crocetin, diapocarotenoic acid, carboxylcarotene, and azafrin.

* * * * *

UNITED STATES PATENT AND TRADEMARK OFFICE
CERTIFICATE OF CORRECTION

PATENT NO. : 6,540,654 B2
DATED : April 1, 2003
INVENTOR(S) : Levy et al.

It is certified that error appears in the above-identified patent and that said Letters Patent is hereby corrected as shown below:

Drawings,
Fig. 2, the last functional group "$COOH_3$" should read -- $COOCH_3$ --, as shown in the attached new Fig. 2.

Signed and Sealed this

Twenty-third Day of November, 2004

JON W. DUDAS
*Director of the United States Patent and Trademark Office*

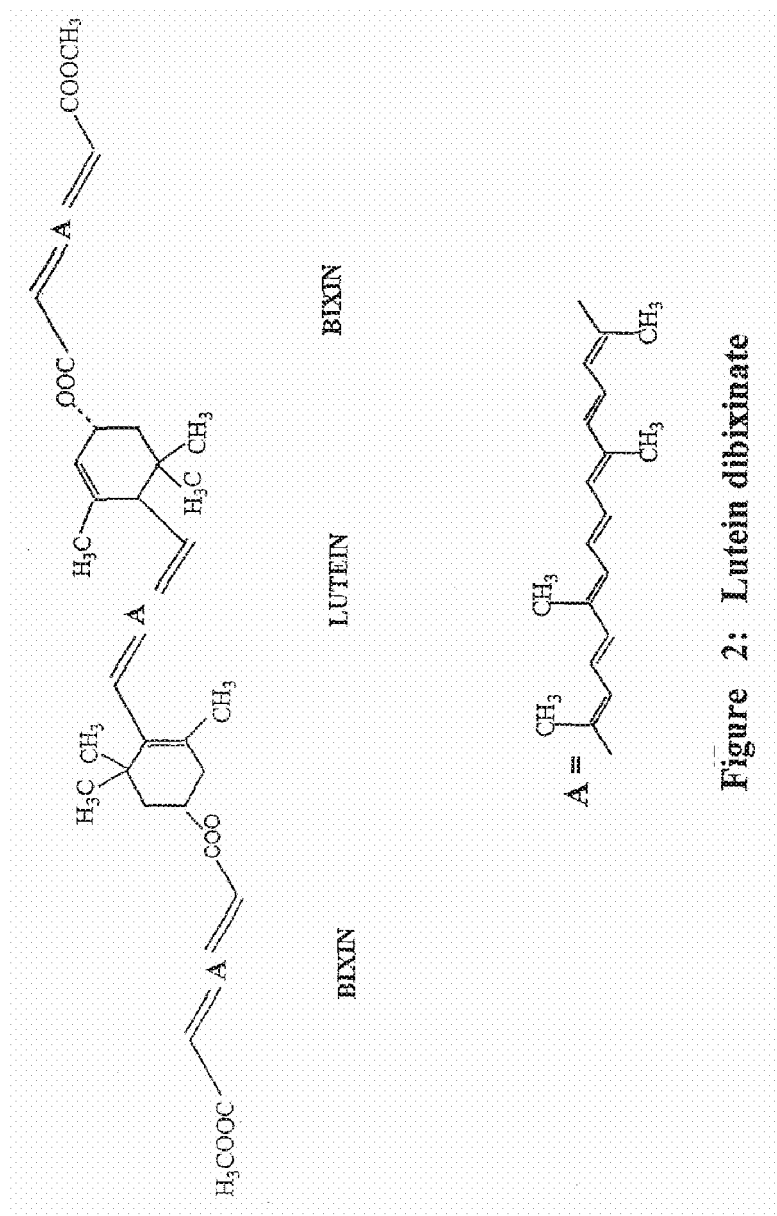
Figure 2: Lutein dibixinate